United States Patent [19]

Cantello et al.

[11] Patent Number: 5,478,851

[45] Date of Patent: Dec. 26, 1995

[54] DIOXOTHIAZOLIDINE COMPOUNDS

[75] Inventors: Barrie C. C. Cantello; David Haigh; Richard M. Hindley, all of Epsom, England

[73] Assignee: Beecham Group plc, United Kingdom

[21] Appl. No.: 50,175

[22] PCT Filed: Oct. 18, 1991

[86] PCT No.: PCT/GB91/01833

§ 371 Date: Apr. 30, 1993

§ 102(e) Date: Apr. 30, 1993

[87] PCT Pub. No.: WO92/07850

PCT Pub. Date: May 14, 1992

[30] Foreign Application Priority Data

Oct. 30, 1990 [GB] United Kingdom ............... 9023584

[51] Int. Cl.$^6$ ..................... C07D 277/34; A61K 31/425
[52] U.S. Cl. ..................... 514/369; 548/183; 546/209; 514/326
[58] Field of Search ............... 548/183; 514/369, 514/326; 546/209

[56] References Cited

U.S. PATENT DOCUMENTS

| | | | |
|---|---|---|---|
| 4,572,912 | 5/1985 | Yoshioka et al. | 514/369 |
| 4,918,091 | 4/1990 | Cantello | 514/369 |
| 5,104,888 | 4/1992 | Yoshioka et al. | 514/369 |
| 5,132,317 | 7/1992 | Cantello | 514/369 |
| 5,330,998 | 7/1994 | Clark | 514/369 |

FOREIGN PATENT DOCUMENTS

| | | |
|---|---|---|
| 0008203 | 2/1980 | European Pat. Off. . |
| 0155845 | 9/1985 | European Pat. Off. . |
| 0177353 | 4/1986 | European Pat. Off. . |
| 0193256 | 9/1986 | European Pat. Off. . |
| 0208420 | 11/1987 | European Pat. Off. . |
| 0295828 | 12/1988 | European Pat. Off. . |
| 0306228 | 3/1989 | European Pat. Off. . |
| 0332331 | 9/1989 | European Pat. Off. . |
| 0415605 | 2/1991 | European Pat. Off. . |
| 0419035 | 3/1991 | European Pat. Off. . |

OTHER PUBLICATIONS

Sohda, Takashi, *Chem Pharm. Bull*, 30(10), pp. 3580–3600, 1982.

Chem. Pharm. Bull., vol. 30, No. 10, 1982, T. Sohda et al.: "Studies on antidiabetic agents. II Synthesis of 5-(4-(1-methylcyclohexylmethoxy)-benzyl)thiazolidine-2,4-dione(ADD-3878) and its derivatives", see p. 3580-p.3600 see p. 3589, lines 10–12; p. 3587, Table V, compounds Nos. 76–80, 82. 1982.

*Primary Examiner*—C. Warren Ivy
*Assistant Examiner*—D. Margaret M. Mach
*Attorney, Agent, or Firm*—Charles M. Kinzig; Stephen Venetianer; Edward T. Lentz

[57] ABSTRACT

It has now been discovered that certain novel amide substituted thiazolidinedione derivatives show improved blood-glucose lowering activity and are therefore of potential use in the treatment and/or prophylaxis of hyperglycaemia and are of particular use in the treatment of Type II diabetes.

10 Claims, No Drawings

DIOXOTHIAZOLIDINE COMPOUNDS

This application is the U.S. National stage of PCT/GB91/10833 filed Oct. 18, 1991.

This invention relates to certain novel compounds, to a process for preparing such compounds, to pharmaceutical compositions containing such compounds and to the use of such compounds and compositions in medicine.

European Patent Applications, Publication Numbers 0008203, 0139421, 0155845, 0177353, 0193256, 0207581 and 0208420 relate to thiazolidinedione derivatives which are disclosed as having hypoglycaemic and hypolipidaemic activity. Chem. Pharm. Bull 30 (10) 3580-3600 also relates to certain thiazolidinedione derivatives having hypoglycaemic and hypolipidaemic activities.

It has now surprisingly been discovered that certain novel amide-substituted thiazolidinedione derivatives show improved blood-glucose lowering activity and are therefore of potential use in the treatment and/or prophylaxis of hyperglycaemia and are of particular use in the treatment of Type II diabetes.

These compounds are also indicated to be of potential use for the treatment and/or prophylaxis of other diseases including hyperlipidaemia, hypertension, cardiovascular disease and certain eating disorders.

Accordingly, the present invention provides a compound of formula (I):

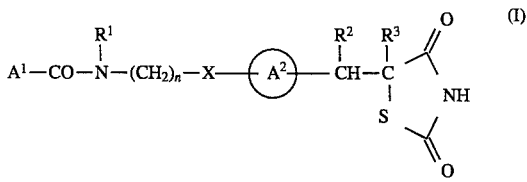

or a tautomeric form thereof and/or a pharmaceutically acceptable salt thereof, and/or a pharmaceutically acceptable solvate thereof, wherein:

$A^1$ represents an alkyl group, a substituted or unsubstituted aryl group, an aralkyl group wherein the alkylene or the aryl moiety may be substituted or unsubstituted or a substituted or unsubstituted aromatic heterocyclyl group;

$A^2$ represents a benzene ring having in total up to three optional substituents;

$R^1$ represents a hydrogen atom, an alkyl group, an aralkyl group wherein the alkyl or the aryl moiety may be substituted or unsubstituted, or a substituted or unsubstituted aryl group;

or $A^1$ together with $R^1$ represents substituted or unsubstituted $C_{3-4}$ polymethylene group, optional substituents for the polymethylene group being selected from alkyl or aryl or adjacent substituents together with the methylene carbon atoms to which they are attached form a substituted or unsubstituted phenylene group;

$R^2$ and $R^3$ each represent hydrogen, or $R^2$ and $R^3$ together represent a bond;

X represents O or S; and n represents an integer in the range of from 2 to 6.

When $A^1$ represents an aryl group, the aryl group is suitably an unsubstituted aryl group, for example a phenyl group.

When $A^1$ represents an aralkyl group, the aralkyl group is suitably a group of formula aryl$(CH_2)_m$, wherein m is 1, 2, 3 or 4, preferably 1 or 2, for example a benzyl group.

When $A^1$ represents an aryl group or an aralkyl group, favoured substituents for the aryl group or the aryl moiety of the aralkyl group are halogen and alkoxy, for example chlorine and methoxy.

Particular examples of $A^1$ include phenyl, benzyl and 2-phenylethyl.

Favourably, $A^1$ together with $R^1$ represents substituted or unsubstituted $C_{3-4}$ polymethylene group, optional substituents for the polymethylene group being selected from alkyl or aryl or adjacent substituents together with the methylene carbon atoms to which they are attached form a substituted or unsubstituted phenylene group.

Favoured substituted or unsubstituted $C_{3-4}$-polymethylene groups include substituted or unsubstituted propylene groups.

Favoured optional substituents for the $C_{3-4}$-polymethylene group, include $C_{1-6}$-alkyl and phenyl groups or adjacent substituents together with the methylene carbon atoms to which they are attached form an optionally substituted phenylene group.

Preferred optional substituents for the $C_{3-4}$ polymethylene group are adjacent substituents which together with the methylene carbon atoms to which they are attached form an optionally substituted phenylene group.

In a particularly favoured aspect, the moiety $A^1$—CO—$NR^1$— represents a 2,3-dihydro-1H-isoindol-1-on-2-yl group or a 3,4-dihydro-2H-isoquinolin-on- 2-yl group wherein the phenylene moiety may be substituted or, most preferably, unsubstituted.

Optional substituents for the phenylene group are selected from: halogen, alkyl, phenyl, alkoxy, haloalkyl, hydroxyalkyl, hydroxy, amino, nitro, cyano, carboxy, alkoxycarbonyl, alkoxycarbonylalkyl, alkylcarbonyloxy and alkylcarbonyl groups.

Preferably, the phenylene group is unsubstituted.

Suitable substituted or unsubstituted aromatic heterocyclyl groups include substituted or unsubstituted, single or fused ring aromatic heterocyclyl groups comprising up to 4 heteroatoms in each ring selected from oxygen, sulphur or nitrogen.

Favoured aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2 or 3 heteroatoms, especially 1 or 2, selected from oxygen, sulphur or nitrogen.

A favoured aromatic heterocyclyl group is a pyridyl group, in particular a 2-pyridyl group.

Suitable substituents for the moiety $A^2$ include halogen, substituted or unsubstituted alkyl or alkoxy.

Favourably, $A^2$ represents a moiety of formula (a):

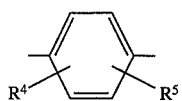

wherein $R^4$ and $R^5$ each independently represent hydrogen, halogen, substituted or unsubstituted alkyl or alkoxy.

Suitably, $R^4$ and $R^5$ each independently represent hydrogen, halogen, unsubstituted alkyl or alkoxy.

Preferably, $R^4$ and $R^5$ each represent hydrogen.

Suitably, $R^1$ represents hydrogen, alkyl or benzyl.

Favourably, $R^1$ represents hydrogen and methyl.

Preferably, $R^1$ represents a methyl group.

Suitably, $R^2$ together with $R^3$ represents a bond.

Preferably, $R^2$ and $R^3$ each represent hydrogen.

In one aspect, X represents sulphur. Preferably, X represents oxygen. Suitably, n represents an integer 2, 3 or 4, notably 2 or 3 and especially 2.

As indicated above a compound of formula (I) may exist in one of several tautomeric forms, all of which are encompassed by the present invention. It will be appreciated that the present invention encompasses all of the isomeric forms of the compounds of formula (I) and the pharmaceutically acceptable salts thereof, including any storeoisomeric forms thereof, whether as individual isomers or as mixtures of isomers.

When used herein the term 'aryl' includes phenyl and naphthyl, preferably phenyl, optionally substituted with up to five, preferably up to three, groups selected from halogen, alkyl, phenyl, alkoxy, haloalkyl, hydroxyalkyl, hydroxy. amino, nitro, cyano, carboxy, alkoxycarbonyl, alkoxycarbonylalkyl, alkylcarbonyloxy, or alkylcarbonyl groups.

Suitable substituents for any heterocyclyl group include up to 4 substituents selected from the group consisting of: alkyl, alkoxy, aryl and halogen or any two substituents on adjacent carbon atoms, together with the carbon atoms to which they are attached, may form an aryl group, preferably a benzene ring, and wherein the carbon atoms of the aryl group represented by the said two substituents may themselves be substituted or unsubstituted.

When used herein the term 'halogen' refers to fluorine, chlorine, bromine and iodine; preferably chlorine.

When used herein the terms 'alkyl' (or 'alk' as used for example in 'alkoxy' or 'alkylene') relate to alkyl groups having straight or branched carbon chains, containing up to 12 carbon atoms.

Suitable alkyl groups are $C_{1-12}$ alkyl groups, especially $C_{1-6}$ alkyl groups e.g. methyl, ethyl, n-propyl, iso-propyl, n-butyl, isobutyl or tert-butyl groups.

Suitable pharmaceutically acceptable salts include salts of the thiazolidinedione moiety, and, where appropriate, salts of carboxy groups.

Suitable pharmaceutically acceptable salts of the thiazolidinedione moiety include metal salts especially alkali metal salts such as the lithium, sodium and potassium salts.

Suitable pharmaceutically acceptable salts of carboxy groups include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-b-phenethylamine, dehydroabietylamine, N,N'-bisdehydroabietylamine, glucamine, N-methylglucamine or bases of the pyridine type such as pyridine, collidine or quinoline.

Suitable pharmaceutically acceptable solvates include hydrates.

In a further aspect the present invention also provides a process for the preparation of a compound of formula (I), or a tautomeric form thereof, and/or a pharmaceutically acceptable salt thereof, and/or a pharmaceutically acceptable solvate thereof, which process comprises reacting a compound of formula (II):

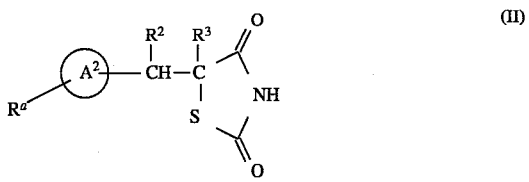

wherein $R^2$, $R^3$ and $A^2$ are as defined in relation to formula (I), and $R^a$ is a moiety convertible to a moiety of formula (b):

$$A^1\text{—CO—NR}^1\text{—(CH}_2)_n\text{—X—} \quad (b)$$

wherein $A^1$, $R^1$, X and n are as defined in relation to formula (I), with an appropriate reagent capable of converting $R^a$ to the said moiety (b) and thereafter, if required, carrying out one or more of the following optional steps:
(i) converting a compound of formula (I) into a further compound of formula (I);
(ii) preparing a pharmaceutically acceptable salt of the compound of formula (I) and/or a pharmaceutically acceptable solvate thereof.

For compounds of formula (I), other than those wherein $A^1$ together with $R^1$ represent a substituted or unsubstituted $C_{3-4}$ polymethylene group, $R^a$ suitably represents $R^{1a}HN\text{—(CH}_2)_n\text{—X—}$ wherein X and n are as defined in relation to formula (I) and $R^{1a}$ represents hydrogen, alkyl or aralkyl, wherein the alkyl or aryl moiety may be substituted or unsubstituted, or substituted or unsubstituted aryl.

Suitably, when $R^a$ is $R^{1a}HN\text{—(CH}_2)_n\text{—X—}$, an appropriate reagent capable of converting $R^a$ into a moiety (b) is a compound of formula (III):

$$A^3\text{—CO—L}^1 \quad (III)$$

wherein $A^3$ is alkyl, substituted or unsubstituted aryl, aralkyl substituted or unsubstituted in the aryl or alkyl moiety or a substituted or unsubstituted heterocyclyl group and $L^1$ represents a leaving group.

A suitable leaving group $L^1$ includes a halogen atom, preferably a chlorine or bromine atom, or an alkoxy group.

The reaction between the compound of formula (II) and the appropriate reagent may be carried out under conditions suitable to the particular compound of formula (II) and the reagent chosen; thus for example the abovementioned reaction between a compound of formula (II) wherein $R^a$ represents $R^{1a}HN\text{—(CH}_2)_n\text{—X—}$ and the compound of formula (III), may be carried out in any suitable solvent, for example tetrahydrofuran, at a temperature in the range of between 0° and 100° C., suitably at 80° C., and preferably in the presence of an organic base, such as triethylamine and/or 4-dimethylaminopyridine and optionally in the presence of trimethylsilylchloride.

Alternatively, $R^a$ represents —XH, wherein X is as defined in relation to formula (I), or $R^a$ represents a leaving group or atom, such as a halogen atom, and especially a fluorine atom.

Preferably, $R^a$ represents —XH, wherein X is defined in relation formula (I).

When $R^a$ represents —XH, a particularly appropiate reagent is a compound of formula (IV);

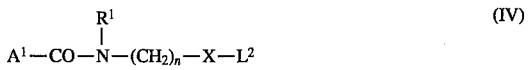

wherein $A^1$, $R^1$, X and n are as defined in relation to formula (I) and $L^2$ represents a leaving group such as a mesyl or tosyl group.

The reaction between the compounds of formulae (II) and (IV) may be carried out in any suitable aprotic solvent, for example dimethylformamide, at any temperature providing a suitable rate of formation of the required product, conveniently at an elevated temperature, for example in the range of from 60° C. to 100° C.; the reaction is generally carried out in the presence of a base, such as sodium hydride and in an inert atmosphere.

When $R^a$ is a leaving group or atom such as a halogen atom, and especially a fluorine atom, a particularly suitable reagent is a compound of formula (VII) as defined hereinafter. Reaction conditions for the reaction between the compounds of formulae (II) wherein $R^a$ is a leaving group or atom, such as halogen and especially fluorine, is analogous to those described hereinafter in relation to the compounds of formulae (V) and (VIIA).

A compound of formula (II) may be prepared by reacting a compound of formula (V):

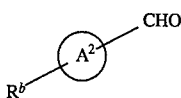   (V)

wherein $A^2$ is as defined in relation to formula (I), and $R^b$ represents $R^a$ or a protected form thereof with 2,4-thiazolidinedione or a protected form thereof; and thereafter, if required, converting a compound of formula (II) wherein $R^2$ and $R^3$ together represent a bond to give a compound of formula (II) wherein $R^2$ and $R^3$ each represent hydrogen and/or removing any protecting group and/or converting one group $R^a$ into another group $R^a$.

The reaction between the compound of formula (V) and 2,4-thiazolidinedione will of course be carried out under conditions suitable to the nature of the compound of formula (V), in general the reaction being carried out in a solvent such as toluene, suitably at an elevated temperature such as the reflux temperature of the solvent and preferably in the presence of a suitable catalyst such as piperidinium acetate or benzoate. Favourably, in the reaction between the compound of formula (V) and 2,4-thiazolidinedione, the water produced in the reaction is removed from the reaction mixture, for example by means of a Dean and Stark apparatus.

For compounds of formula (II) wherein $R^a$ is HX—, $R^b$ suitably represents a protected form of $R^a$, for example a group $R^cX$— where $R^c$ is a benzyl group.

The interconversion of one group $R^a$ into another may be effected by any suitable procedure: for example a compound of formula (II) wherein $R^a$ is $R^{1a}$HN—$(CH_2)_n$—X— may be prepared from the corresponding compound of formula (II) wherein $R^a$ is —XH; thus the appropriate conversion may be carried out by coupling a compound of formula (IIA):

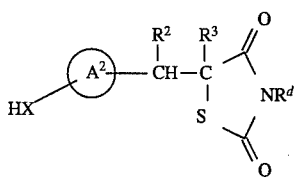   (IIA)

wherein $R^2$, $R^3$, $A^2$ and X are as defined in relation to formula (I) and $R^d$ is hydrogen or a nitrogen protecting group, with a compound of formula (VI):

   (VI)

wherein $R^{1a}$ and n are as defined above and $R^e$ is hydrogen or a nitrogen protecting group, in the presence of a suitable coupling agent; and thereafter, if required, carrying out one or more of the following optional steps:
(i) reducing a compound of formula (II) wherein $R^2$ and $R^3$ together represent a bond, to a compound of formula (II) wherein $R^2$ and $R^3$ each represent hydrogen;
(ii) removing any nitrogen protecting group.

A suitable coupling agent for the coupling reaction between the compound of formula (IIA) and (VI) is provided by diethylazodicarboxylate and triphenylphosphine. The coupling reaction may be carried out in any suitable solvent at a low to medium temperature, for example in tetrahydrofuran at a temperature in the range of between 0° and 60° C.

A compound of formula (IV) may be prepared by suitable conversion of a compound formula (VII):

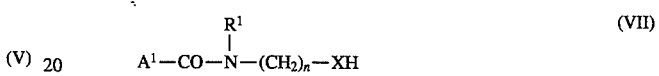   (VII)

wherein $A^1$, $R^1$, X and n are as defined in relating to formula (I); for example when $L^2$ in (IV) represents mesyl or tosyl group the suitable conversion may be effected by mesylation or tosylation, as appropriate, in an inert solvent such as dichloromethane at any temperature providing a suitable rate of formation of the required product, conveniently at room temperature or lower, for example at 0° C., and preferably in the presence of a base such as triethylamine.

A compound of formula (VII) wherein $A^1$ represents alkyl, substituted or unsubstituted aryl, an aralkyl group substituted or unsubstituted in the alkyl or aryl moiety or $A^1$ represents —Y—B wherein Y is a bond or an alkylene group and B represents a substituted or unsubstituted aromatic heterocyclyl group and $R^1$ represents $R^{1a}$, as defined above, may be prepared by reacting a compound of the hereinbefore defined formula (III) with a compound of formula (VIII):

   (VIII)

wherein $R^1a$ and n are as defined above.

The reaction between the compounds of formulae (III) and (VIII) may be carried out using conventional peptidation conditions: the reaction is conveniently effected in a biphasic solvent system such as water/chloroform or in water only in the presence of a base such as sodium carbonate, or sodium hydroxide at a temperature providing a convenient rate of formation of the required product, suitably at room temperature or lower, for example at 0° C. Alternatively, where convenient, the compound of formula (VIII) may be used as solvent, the reaction being carried out at an elevated temperature, suitably a.t the reflux temperature of the solvent: This latter variation of the reaction is particularly suitable when the compound of formula (VIII) is an ethanolamine.

A compound of formula (VII) wherein $A^1$ together with $R^1$ represents a substituted or unsubstituted $C_{3-4}$-polymethylene group, as defined in relation to formula (I), may be prepared by reacting a compound of formula (IX):

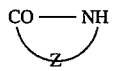

wherein Z represents the substituted or unsubstituted $C_{3-4}$-polymethylene group as defined in relation to formula (I), with a compound of formula (X):

wherein n and X are as defined in relation to formula (I), $L^3$ represents a leaving group, preferably a bromine atom, and $R^f$ represents hydrogen or a protecting group.

The reaction between compounds of formulae (IX) and (X) may be carried out in any suitable aprotic solvent, such as dimethylformamide, at any temperature providing a suitable rate of formation of the required product, suitably at a temperature in the range of from 0° to 100° C., for example 80° C. and preferably in the presence of a base such as potassium carbonate or sodium hydride.

Preferably, X represents O.

A compound of formula (I), or a tautomeric form thereof, and/or a pharmaceutically acceptable salt thereof and/or a pharmaceutically acceptable solvate thereof, may also be prepared by reacting a compound of formula (XI):

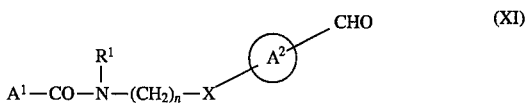

wherein $R^1$, $A^1$, $A^2$, X and n are as defined in relation to formula (I) with (XI) 2,4-thiazolidinedione; and thereafter if required carrying out one or more of the following optional steps:
(i) converting a compound of formula (I) into a further compound of formula (I);
(ii) preparing a pharmaceutically acceptable salt of a compound of formula (I) and/or a pharmaceutically acceptable solvate thereof.

The reaction between the compound of formula (XI) and 2,4-thiazolidinedione will of course be carried out under conditions suitable to the nature of the compound of formula (XI), in general the reaction being carried out in a solvent such as toluene, suitably at an elevated temperature such as the reflux temperature of the solvent and preferably in the presence of a suitable catalyst such as piperidinium acetate or benzoate. Favourably, in the reaction between the compound of formula (XI) and 2,4-thiazolidinedione, the water produced in the reaction is removed from the reaction mixture, for example by means of a Dean and Stark apparatus.

A compound of formula (XI) may be prepared from a compound of formula (V), or a protected form thereof, wherein $R^b$ represents $R^a$, by reaction, with an appropriate reagent capable of converting $R^a$ to the above defined moiety (b).

Suitable values for $R^a$ include those described above in relation to the compound of formula (II). Appropriate reagents are also described above in relation to formula (II).

Suitable reaction conditions for the reaction of the compound of formula (V) and the appropriate reagent include those described above in relation to the preparation of compound (II) with the said appropriate reagent.

Suitable protected forms of compounds of formula (V) include those wherein the aldehyde group is protected. Suitable protecting groups are those used conventionally in the art. It has been found convenient to protect the aldehyde group by reducing it to a hydroxymethyl group, deprotection is conveniently effected by oxidation back to the aldehyde. Suitable reducing agents are conventional agents such as complex metal hydride reducing agents such as lithium aluminium hydride or as appropriate, the use of a zinc powder/acetic acid reducing agent. Suitable oxidising agents are conventional oxidising agents such as $Mn^{IV}O_2$.

In one preferred aspect for preparing compounds of formula (XI), $R^b$ in compound (V) represents a leaving group or atom, especially a fluorine atom: When $R^b$ represents a leaving group or atom, especially a fluorine atom, a particularly appropriate reagent is a compound of the above defined formula (VII):

The reaction between the compounds of formulae (V) and (VII) may be carried out under any suitable conditions, for example in a solvent such as dimethylformamide or dimethylsulphoxide at an elevated temperature for example in the range of from 60° to 150° C., suitably in the presence of a base such as sodium hydride, sodium hydroxide or potassium carbonate and preferably in an inert atmosphere such as nitrogen.

In a further aspect, when $R^b$ in the compound of formula (V) represents a moiety of the above defined formula $R^{1a}HN(CH_2)_nX—$, then a particularly appropriate reagent is a compound of the abovedefined formula (III).

The reaction between the compound of formula (V), wherein $R^a$ is a moiety $R^{1a}HN(CH_2)_2—X—$, and the reagent of formula (III) is generally carried out under conditions analogous to those disclosed above in relation to the reaction between the compounds of formlulae (II) and (III).

Preferably in the abovementioned reaction, the aidehyde group of the compound of formula (V) is in a protected form: a convenient protected form is provided by reducing the aldehyde to a hydroxymethyl group, as described herein, and thereafter oxidising the hydroxymethyl group to the aldehyde as described herein.

Compounds of formula (V) wherein $R^b$ is a protected form of $R^a$ may be prepared from the corresponding compound of formula (V) wherein $R^b$ is $R^a$.

The compounds of formula (V) wherein $R^b$ is hydroxyl or fluorine are known compounds or compounds prepared by methods analogous to those used to prepare known compounds, for example 4-fluorobenzaldehyde and 4-hydroxybenzaldehyde are known commercially available compounds and the compounds of formula (V) wherein $R^b$ is SH are prepared according to methods disclosed in Beilstein 8.I.533.

The abovementioned conversion of a compound of formula (I) into a further compound of formula (I) includes the following conversions:
(a) reducing a compound of formula (I) wherein $R^2$ and $R^3$ together represent a bond, to a compound of formula (I) wherein $R^2$ and $R^3$ each represent hydrogen; and
(b) converting one group $R^1$ into another group $R^1$.

The conversion of a compound of formula (I) to a further compound of formula (I) may be carried out by using any appropriate conventional procedure.

A suitable reduction method for the abovementioned conversion (a) includes catalytic reduction or the use of a metal/solvent reducing system.

Suitable catalysts for use in the catalytic reduction are palladium on carbon catalysts, preferably a 10% palladium on charcoal catalyst; the reduction being carried out in a solvent, for example dioxan, suitably at ambient temperature.

Suitable metal/solvent reducing systems include magnesium in methanol.

The abovementioned reduction of a compound of formula (II) wherein $R^2$ and $R^3$ together represent a bond to a compound of formula (II) wherein $R^2$ and $R^3$ each represent hydrogen, may be carried out under analogous conditions to those referred to above in conversion (a) of the compound of formula (I).

In the abovementioned conversion (b), suitable conversions of one group $R^1$ into another group $R^1$ includes converting a group $R^1$ which represents hydrogen into a group $R^1$ which represents an alkylgroup.

The conversion of a compound of formula (I) wherein $R^1$ represents hydrogen into a compound of formula (I) wherein $R^1$ represents alkyl may be carried out using any appropriate conventional alkylation procedure, such as by treating an appropriately protected compound of formula (I) with an alkyl halide, for example an alkyl iodide.

It will be appreciated that in the abovementioned conversions (a) and (b), any reactive group in the compound of formula (I) would be protected, according to conventional chemical practice, where necessary.

The compounds of formula (III), (VIII), (VIIIA) and (X) are either known compounds or are prepared using methods analogous to those used to prepare known compounds for example methods disclosed in Advanced Organic Chemistry, J. March, McGraw Hill.

A compound of formula (VI), wherein $R^e$ is a nitrogen protecting group, may be prepared by suitably protecting the nitrogen atom of a compound of the abovedefined formula (VIII).

Suitable protecting groups in any of the abovementioned reactions are those used conventionally in the art. Thus, for example, a suitable nitrogen protecting group is a benzyl group or a benzyloxycarbonyl group and a suitable hydroxyl protecting group is a benzyl group.

Suitable protecting groups in any of the abovementioned reactions are those used conventionally in the art. Thus, for example, a suitable nitrogen protecting group is a benzyl group or a benzyloxycarbonyl group or, especially for the thiazolidinedione nitrogen, a trimethylsilyl group or an allyl group and a suitable hydroxyl protecting group is a benzyl group.

The methods of formation and removal of such protecting groups are those conventional methods appropriate to the molecule being protected. Thus for example an N— benzyl group may be prepared by treatment of the appropriate amine with a benzyl halide, such as benzyl bromide, and thereafter when required the benzyl group may be conveniently removed using catalytic hydrogenation.

Where appropriate the isomeric forms of the compounds of formula (I) and the pharmaceutically acceptable salts thereof may be prepared as individual isomers using conventional chemical procedures.

Pharmaceutically acceptable salts and/or solvates of the compounds of formula (I) may be prepared according to conventional procedures.

As mentioned above the compounds of the invention are indicated as having useful therapeutic properties:

The present invention accordingly provides a compound of formula (I), or a tautomeric form thereof and/or a pharmaceutically acceptable salt thereof and/or a pharmaceutically acceptable solvate thereof, for use as an active therapeutic substance.

Thus the present invention provides a compound of formula (I), or a tautomeric form thereof and/or a pharmaceutically acceptable salt thereof and/or a pharmaceutically acceptable solvate thereof, for use in the treatment of and/or prophylaxis of hyperglycaemia.

In a further aspect the present invention also provides a compound of formula (I), or a tautomeric form thereof and/or a pharmaceutically acceptable salt thereof and/or a pharmaceutically acceptable solvate thereof, for use in the treatment and/or prophylaxis of hyperlipidaemia.

As indicated hereinbefore the present invention also provides a compound of formula (I) or a taummeric form thereof and/or a pharmaceutically acceptable salt thereof and/or a pharmaceutically acceptable solvate thereof for use in the treatment of hypertension, cardiovascular disease and certain eating disorders.

A compound of formula (I), or a tautomeric form thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising acompound of the general formula (I), or a tautomeric form thereof, or a pharmaceutically acceptable salt thereof, or a pharmaceutically acceptable solyarc thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of the general formula (I), or a tautomeric form thereof and/or a pharmaceutically acceptable salt thereof and/or a pharmaceutically acceptable solvate thereof to a hyperglycaemic human or non-human mammal in need thereof.

The present invention further provides a method for the treatment of hyperlipidaemia in a human or non-human mammal, which comprises administering an effective, non-toxic, amount of a compound of formula (I), or a tautomeric form thereof and/or a pharmaceutically acceptable salt thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the compound of the general formula (I), or a tautomeric form thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be administered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The dosages regimens for the treatment of hypertension, cardiovascular disease and eating disorders will generally be those mentioned above in relation to hyperglycaemia.

In a further aspect the present invention provides the use of a compound of formula (I), or a tautomeric form thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

The following Procedures and Examples illustrate the invention but do not limit it in any way..

PROCEDURE 1

2-(N-Benzoyl-N-methylamino)ethanol

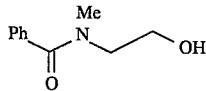

Ethyl benzoate (16.0 g, 15.3 ml) was dissolved in 2-(N-methylamino)ethanol (200 ml) and the mixture heated at reflux for 17.5 hours, cooled and diluted with water (1 l). The mixture was extracted with dichloromethane (4×200 ml), and the combined dichloromethane solutions washed with brine (300 ml), dried (MgSO$_4$) and evaporated. The title compound, an oil, was used without further purification.

$^1$H NMR δ(CDCl$_3$)

Some peaks in this spectrum are complicated by the presence of rotational isomers of the amide group.

3.05 (3H, s); 3.25 (1H, s, exchanges with D$_2$O); 3.50–4.00 (4H, broad); and 7.52 (5H, s).

PROCEDURE 2

4-[2-(N-Benzoyl-N-methylamino)ethoxy]benzaldehyde

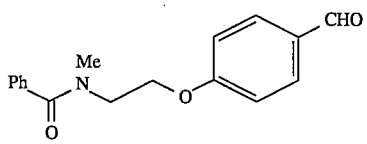

Sodium hydride (60% dispersion in oil, 1.30 g) was added portionwise to a solution of 2-(N-benzoyl-N-methylamino)ethanol (5.0 g) in dry dimethylformamide (100 ml) at room temperature under a nitrogen atmosphere. The mixture was stirred at room temperature for 1 hour prior to the addition of 4-fluorobenzaldehyde (5.09 g, 4.4 ml), and the mixture then heated at 80° C. for 15 hours. The solvent was evaporated and the residue dissolved in water (500 ml) and extracted with ethyl acetate (3×500 ml). The combined ethyl acetate layers were washed with water (2×300 ml), brine (300 ml), dried (MgSO$_4$) and evaporated to yield an oil. The oil was triturated with hexane, and the residue chromatographed on silica gel with 1.5% methanol in dichloromethane to afford the title compound as an oil.

$^1$H NMR δ(CDCl$_3$)

Some peaks in this spectrum are complicated by the presence of rotational isomers of the amide group.

3.15 (3H, s); 3.85 (2H, apparent broad s); 4.30 (2H, apparent broad s); 7.00 (2H, br d); 7.47 (5H, s); 7.91 (2H, d); 9.97 (1H, s).

PROCEDURE 3

2-(N-(5-Chloro-2-methoxybenzoyl)amino)ethanol

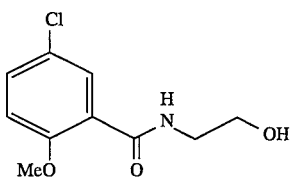

5-Chloro-2-methoxybenzoyl chloride (5.0 g) was added to a vigorously stirred mixture of 2-aminoethanol (10.12 g, 10 ml) and sodium hydroxide solution (1M, 100 ml). Stirring was continued for 2 hours at room temperature, then dilute hydrochloric acid (10% v/v, 100 ml) was added and the mixture extracted with dichloromethane (3×200 ml). The combined dichloromethane layers were dried (MgSO$_4$) and evaporated, and the resulting oil chromatographed on silica gel with 1% methanol in dichloromethane as solvent to afford the title compound as an oil.

$^1$H NMR δ(CDCl$_3$)

3.30–3.80 (5H, complex; reduced to 4H on shaking with D$_2$O); 3.90 (3H, s); 6.83 (1H, d); 7.32 (1H, dd); 8.05 (1H, d); and 8.27 (1H, broad, exchanges with D$_2$O).

PROCEDURE 4

4-[2-(N-(5-Chloro-2-methoxybenzoyl)amino)ethoxy]-benzaldehyde

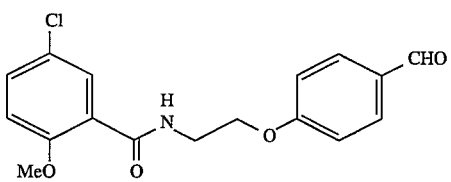

A mixture of 2-(N-(5-chloro-2-methoxybenzoyl)amino)ethanol (4.5 g), potassium carbonate (5 g) and 4-fluorobenzaldehyde (2.5 g, 2.16 ml) were heated at 100° C. in dry dimethylsulphoxide (50 ml) for 18 hours. The mixture was cooled, diluted with water and extracted with diethyl ether containing a little methanol. The organic layers were combined, dried (MgSO$_4$) and evaporated. The residual oil was chromatographed on silica gel with 2% methanol in dichloromethane as solvent to afford the title compound as an oil.

$^1$H NMR δ(CDCl$_3$)

3.70–4.05 (5H, complex); 4.22 (2H, t); 6.75–7.15 (3H, complex); 7.40 (1H, dd); 7.83 (2H, d); 8.17 (1H, d); 8.20 (1H, br, exchanges with D$_2$O); and 9.90 (1H, s).

PROCEDURE 5

2-(N-Methyl-N-phenylacetylamino)ethanol

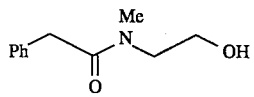

The title compound, an oil, was prepared from ethyl phenylacetate (16.5 g, 16 ml) by a procedure similar to that described in Procedure 1.

$^1$H NMR δ(CDCl$_3$)

This spectrum is complicated by the presence of rotational isomers of the amide group.

2.90–3.20 (4H, complex; reduced to 3H on shaking with D$_2$O); 3.30–3.90 (6H, complex); and 7.37 (5H, s).

PROCEDURE 6

4-[2-(N-Methyl-N-phenylacetylamino)ethoxy]-benzaldehyde

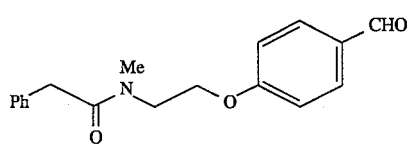

The title compound, an oil, was obtained when 2-(N-methyl-N-phenylacetylamino)ethanol (7.72 g) was reacted with 4-fluorobenzaldehyde (7.52 g, 6.5 ml) by a method analogous to that described in Procedure 2.

$^1$H NMR δ(CDCl$_3$)

This spectrum is complicated by the presence of rotational isomers of the amide group.

3.05 and 3.15 (combined, 3H, singlets); 3.60–4.30 (6H, complex); 7.00 (2H, br d); 7.32 (5H, s); 7.88 (2H, d); and 9.95 (1H, s).

PROCEDURE 7

4-[2-(N-Methyl-N-(2-pyridyl)acetylamino)ethoxy]-benzaldehyde

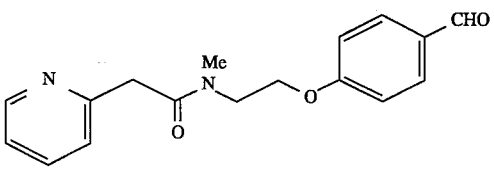

Methyl 2-pyridylacetate (10.0 g, 8.9 ml) was dissolved in 2-(N-methylamino)ethanol (150 ml) and the mixture heated at reflux for 84 hours, then cooled and concentrated under reduced pressure. The residue was dissolved in water (100 ml) and continuously extracted overnight with ethyl acetate. The ethyl acetate solution was dried (MgSO$_4$) and evaporated to afford an oil which no longer displayed an ester signal (δ3.70) in the nmr spectrum. The oil was dissolved in dry dimethylformamide (150 ml) at room temperature under a nitrogen atmosphere, and sodium hydride (60% dispersion in oil, 3.42 g) was added. The mixture was stirred for 1 hour, then 4-fluorobenzaldehyde (10.6 g, 9.2 ml) was added and the mixture heated at 80° C. for 22.5 hours, cooled, diluted with water (1 l) and extracted with ethyl acetate (3×400 ml). The combined ethyl acetate layers were washed with water (3×1 l) and brine (1 l), dried (MgSO$_4$) and evaporated. The resulting oil was triturated with hexane and the residue chromatographed on silica gel with 1.5% methanol in dichloromethane as solvent to afford the title compound as an oil.

$^1$H NMR δ(CDCl$_3$)

Some peaks in this spectrum are complicated by the presence of rotational isomers of the amide group.

3.03 and 3.25 (combined, 3H, singlets); 3.60–4.40 (6H, complex); 6.95 (2H, d); 7.00–7.75 (3H, complex); 7.85 (2H, d); 8.50 (1H, d); and 9.95 (1H, s).

PROCEDURE 8

4-(2-Phthalimidoethoxy)benzaldehyde

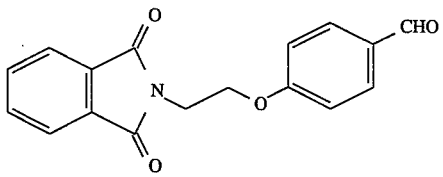

The title compound, mp 138° C., was prepared from N-(2-hydroxyethyl)phthalimide (9.6 g) and 4-fluorobenzaldehyde (6.2 g, 5.3 ml) by a procedure similar to that described in Procedure 2.

$^1$H NMR δ(CDCl$_3$)

4.05 (2H, t); 4.33 (2H, t); 7.10 (2H, d); 7.70–8.10 (6H, complex); and 9.82 (1H, s).

PROCEDURE 9

4-[2-(2.3-Dihydro-1H-isoindol-1-on-2-yl)ethoxy]benzyl alcohol

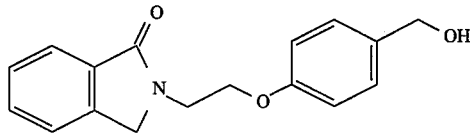

4-(2-Phthalimidoethoxy)benzaldehyde (6.8 g) was dissolved in glacial acetic acid (70 ml) at 60° C. Powdered zinc (9.1 g) was added, and the mixture heated at reflux and stirred vigorously for 18.25 hours before being filtered whilst hot, and allowed to cool to room temperature. The acetic acid was evaporated and the resulting gum dissolved in methanol (75 ml). Sodium hydroxide solution (10% w/v; 75 ml) was added, and the mixture stirred for 2 hours at room temperature, diluted with water (1 l), acidified to pH4 with hydrochloric acid, and then continuously extracted with dichloromethane for 3 hours. The dichloromethane layer was evaporated and the residue chromatographed on silica gel using 1.5% methanol in dichloromethane to afford the title compound, mp 106°–107° C.

$^1$H NMR δ(CDCl$_3$)

2.75 (1H, s, exchanges with D$_2$O); 3.93 (2H, t); 4.17 (2H, t); 4.60 (4H, apparent s); 6.85 (2H, d); and 7.10–7.90 (6H, complex).

PROCEDURE 10

4-[2-(2.3-Dihydro-1H-isoindol-1-on- 2-yl)ethoxy]benzaldehyde

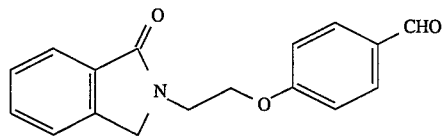

A mixture of 4-[2-(2,3-dihydro-1H-isoindol-1-on-2-yl)-ethoxy]benzyl alcohol (2.97 g), manganese(IV) oxide (9.12 g) and dichloromethane (180 ml) was stirred for 3 hours at room temperature. The mixture was filtered through a Soxhlet thimble and the residue extracted with refluxing dichloromethane for 3 hours. The solvent was then evaporated to afford the title compound, mp 134°–135° C.

$^1$H NMR δ(CDCl$_3$)

4.03 (2H, t); 4.32 (2H, t); 4.60 (2H, s); 7.10 (2H, d); 7.55 (3H, complex); 7.85 (3H, complex); and 9.95 (1H, s).

PROCEDURE 11

3-Phthalimidopropanol methanesulphonyl ester

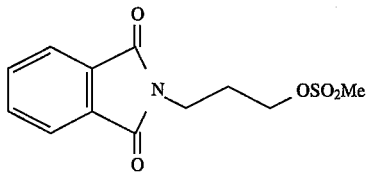

Methanesulphonyl chloride (5.72 g; 4.25 ml) was added dropwise to a stirred, ice cooled mixture of N-(3-hydroxypropyl)phthalimide (10.26 g) and triethylamine (6.09 g, 8.4 ml) in dichloromethane (250 ml). The mixture was stirred at 0° C. for 1.5 hours, then washed with water (3×300 ml), saturated sodium bicarbonate solution (300 ml), and brine (300 ml), dried (MgSO$_4$) and evaporated. The title compound, mp 133°–135° C., was used without further purification.

$^1$H NMR δ (CDCl$_3$)

2.15 (2H, complex); 3.05 (3H,s); 3.82 (2H,t); 4.25 (2H, t); and 7.50–7.90 (4H, complex).

Procedure 12

4-(3-Phthalimidopropoxy)benzaldehyde

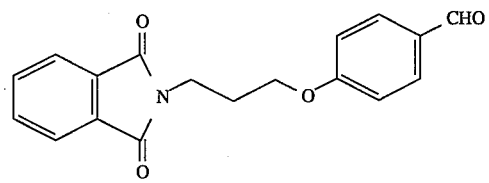

Sodium hydride (60% disperion in oil, 2.01 g) was added to a stirred solution of 4-hydroxybenzaldehyde (5.25 g) in dry dimethylformamide (100 ml) under a nitrogen atmosphere at room temperature, and the mixture stirred for 30 minutes. A solution of 3-phthalimidopropanol methanesulphonyl ester (12.2 g) in dry dimethylformamide (200 ml) was added, and stirring continued at 80° C. for 14.5 hours. After cooling the mixture was diluted with water (2 l) and extracted with ethyl acetate (4×400 ml). The combined organic layers were washed with water (4×1 l) and brine (1 l), dried (MgSO$_4$) and evaporated. Chromatography on silica gel with dichloromethane as solvent afforded the title compound, mp 122-5° C.

$^1$H NMR δ (CDCl$_3$)

2.27 (2H, complex); 3.95 (2H, t); 4.13 (2H, t); 6.95 (2H, d); 7.60–8.20 (6H, complex); and 9.95 (1H, s).

Procedure 13

4-[3-(2,3-Dihydro-1H-isoindol-1-on-2-yl)propoxy]benzyl alcohol

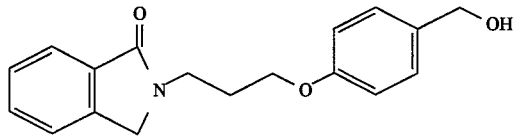

The title compound, mp 121-4° C., was prepared from 4-(3-phthalimido propoxy)benzaldehyde (9.27 g) by a method analogous to that described in Procedure 9.

$^1$H NMR δ (CDCl$_3$)

2.10 (2H, complex); 2.63 (1H, s, exchanges with D$_2$O); 3.70 (2H, t); 3.95 (2H, t); 4.35 (2H, s); 4.55 (2H, s); 6.77 (2H, d); and 7.10–7.90 (6H, complex).

Procedure 14

4-[3-(2,3-Dihydro-1H-isoindol-1-on-2-yl)propoxy]benzaldehyde

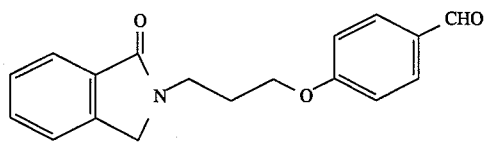

The title compound, mp 113-5° C., was prepared from 4-[3-(2,3-dihydro-1H-isoindol- 1-on-2-yl)propoxy]benzyl alcohol (4.41 g) by a method analogous so that described in Procedure 10.

$^1$H NMR d (CDCl$_3$)

2.17 (2H, complex); 3.80 (2H, t); 4.10 (2H, t); 4.40 (2H, s); 6.95 (2H, s); 7.50 (3H, complex); 7.75 (3H, complex); and 9.92 (1H, s).

Procedure 15

4-(2-Hydroxyethoxy)benzaldehyde methanesulphonyl ester

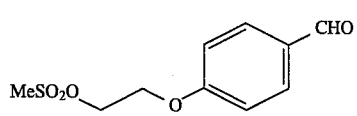

4-(2-Hydroxyethoxy)benzaldehyde (14.1 g) was reacted with methanesulphonyl chloride (10.7 g; 7.23 ml) in a manner analogous to that described in Procedure 11. The crude product was chromatographed on silica gel with 1.5% methanol in dichloromethane as solvent to afford the title compound, mp 66-7° C.

$^1$H NMR δ (CDCl$_3$)

3.10 (3H, s); 4.37 (2H, t); 4.60 (2H, t); 7.07 (2H, d); 7.90 (2H, d); and 9.95 (1H,s).

Procedure 16

4-[2-(3,4-Dihydro-2H-isoquinolin-1-on-2-yl)ethoxy]benzaldehyde

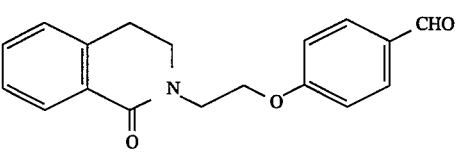

3,4-Dihydro-2H-isoquinolin-1-one (5.14 g) was dissolved in dry tetrahydrofuran (100 ml) at 0° C. under a nitrogen atmosphere and treated with sodium hydride (60% dispersion, 1.54 g). The mixture was allowed to warm to room temperature over 30 minutes prior to the addition of a solution of 4-(2-hydroxyethoxy)benzaldehydemethanesulphonyl ester (8.54 g) in tetratrydrofuran (150 ml). After stirring the mixture at room temperature for 15 minutes, it was heated at reflux for 23 hours, cooled and evaporated. The residue was suspended in water (1l), acidified with dilute hydrochloric acid, and then extracted with ethyl acetate (3×400 ml). The combined organic layers were washed with water (1l), brine (1l), dried (MgSO$_4$) and evaporated. The residue was chromatographed on silica gel with 1% methanol in dichloromethane as solvent to afford the title compound, mp 131-4° C.

$^1$H NMR δ (CDCl$_3$)

2.95 (2H, apparent t); 3.60–4.10 (4H, complex); 4.30 (2H, t); 6.85–7.55 (5H, complex); 7.80 (2H, d); 8.00 (1H, complex); and 9.83 (1H, s).

Procedure 17

4-(N-Methylaminocarbonylmethoxy)benzaldehyde

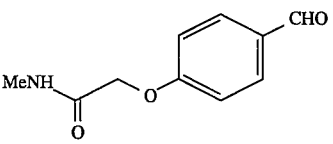

4-(Methoxycarbonylmethoxy)benzaldehyde (19.5 g was dissolved in a solution of methylamine in ethanol (8M; 300 ml). The flask was sealed and kept at room temperature for 18.5 hours before being opened and the contents evaporated. The residue was dissolved in ethanol (100 ml) and dilute hydrochloric acid (200 ml) and stirred at room temperature for 3 hours before being continuously extracted with dichloromethane for 6 hours. Evaporation of the dried (MgSO$_4$) dichloromethane solution afforded the title compound, mp 122-5° C. which was used without further purification.

$^1$H NMR δ (CDCl$_3$)

2.95 (3H, apparent d); 4.65 (2H, s); 6.83 (1H, broad s); 7.13 (2H, d); 7.95 (2H, d); and 10.05 (1H, s).

Procedure 18

4-[2-(Methylamino)ethoxy]benzyl alcohol

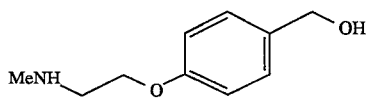

A solution of 4-(N-methylaminocarbonylmethoxy-)benzaldehyde (9.65 g) in dry tetrahydrofuran (300 ml) was added slowly to a stirred, ice-cooled suspension of lithium aluminium hydride (9.5 g) in dry tetrahydrofuran (100 ml) under a nitrogen atmosphere. The resulting mixture was warmed at reflux for 12 hours, then cooled in ice during the addition of water (9.5 ml), 10% aqueous sodium hydroxide (9.5 ml) and water (28.5 ml). The mixture was heated at reflux for 10 minutes, then filtered through a Soxhlet thimble and the residue Soxhlet extracted with tetrahydrofuran. Evaporation of the combined tetrahydrofuran layers afforded the title compound as an oil which was used without further purification.

$^1$H NMR δ (CDCl$_3$)

2.40 (3H, s); 2.95 (2H, t); 3.21 (2H, br s, exchanges with D$_2$O); 4.05 (2H, t); 4.65 (2H, s); 6.90 (2H, d); and 7.35 (2H, d).

Procedure 19

4-[2-[N-Methyl-N-(3-phenylpropanoyl)amino]ethoxy] benzyl alcohol

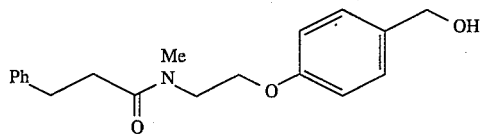

Trimethylsilyl chloride (2.17 g, 2.54 ml) was added to an ice-cooled solution of 4-[2-(methylamino)ethoxy]benzyl alcohol (3.78 g), triethylamine (4.50 g, 6.2 ml) and 4-dimethylaminopyridine (0.4 g) in dichloromethane (200 ml). The mixture was stirred at 0° C. for 1.5 hours prior to the addition of 3-phenylpropanoyl chloride (3.37 g, 2.97 ml), and the mixture then stirred at room temperature for 16 hours. Hydrofluoric acid (48%, 1 ml) was added and the mixture stirred at room temperature for 15 minutes, then diluted with dilute hydrochloric acid (50 ml) and stirred for a further 3.5 hours. Water (200 ml) was added and the layers separated. The organic layer was washed with saturated sodium bicarbonate solution (400 ml), water (2–400 ml), brine (400 ml), dried (MgSO$_4$) and evaporated. The residue was chromatographed on silica gel with 1.5% methanol in dichloromethane to afford the title compound as an oil.

$^1$H NMR δ (CDCl$_3$)

This spectrum is complicated by the presence of rotational isomers of the amide group.

2.40–3.00 (5H, complex; reduced to 4H on shaking with D$_2$O); 3.00 and 3.10 (combined, 3H singlets); 3.60 and 3.70 (combined, 2H, rotameric triplets); 4.62 (2H, s); and 6.70–7.40 (9H, complex).

Procedure 20

4-[2-[N-Methyl-N-(3-phenylpropanoyl)amino]ethoxy] benzaldehyde

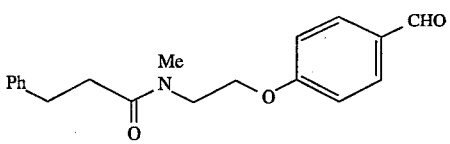

4-[2-[N-Methyl-N-(3-phenylpropanoyl)amino]ethoxy] benzyl alcohol (3.40 g) was oxidised with manganese (IV) oxide (9.4 g) in a manner analogous to that described in Procedure 10, to afford the title compound as a gum.

$^1$H NMR δ (CDCl$_3$)

This spectrum is complicated by the presence of rotational isomers of the amide group.

2.50–3.20 (7H, complex); 3.75 (2H, broad apparent triplet); 3.95–4.30 (2H, complex); 6.93

(2H, broad d); 7.17 (5H, s); 7.77 (2H, d); and 9.85 (1H, s).

Example 1

5-(4-[2-(N-Benzoyl-N-methylamino)ethoxy]benzylidene)- 2,4-thiazolidinedione.

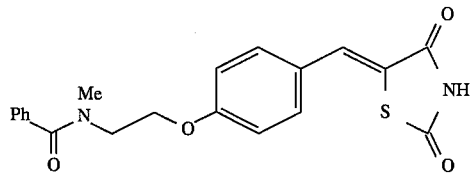

A mixture of 4-[2-(N-benzoyl-N-methylamino)ethoxy] benzaldehyde (3.94 g), 2,4-thiazolidinedione (1.79 g), benzoic acid (0.2 g) and piperidine (0.2 ml) were heated at reflux in toluene (250 ml) in a Dean and Stark apparatus. After 5 hours at reflux the mixture was allowed to cool and crystallise overnight. The title compound, mp 178-180° C., was filtered off, washed with cold toluene and dried under vacuum.

$^1$H NMR δ (DMSO-d$_6$; 80° C.)

This spectrum is complicated by the presence of rotational isomers of the amide group. These coalesce at 80° C. 3.01 (3H, s); 3.75 (2H, t); 4.26 (2H, t); 7.07 (2H, d); 7.30–7.60 (7H, complex); 7.71 (1H, s); and 12.25 (1H, br s, exchanges with D$_2$O).

Example 2

5-(4-[2-(N-Benzoyl-N-methylamino)ethoxy]benzyl)-2,4-thiazolidinedione.

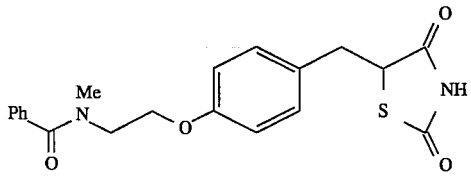

5-(4-[2-(N-Benzoyl-N-methylamino)ethoxy]benzylidene)-2,4-thiazolidinedione (4.01 g) was dissolved in dioxan (400 ml) and hydrogenated at room temperature and pressure in the presence of 10% palladium-charcoal (4 g) for 3.5 hours. A further portion of catalyst (4 g) was added, and the reaction continued for a total of 52 hours. The reaction mixture was filtered through diatomaceous earth, and the solvent evaporated. The resulting gum was recrystallised from dichloromethane-diethyl ether to afford the title compound, mp 139-142° C.

$^1$H NMR δ (CDCl$_3$)

This spectrum is complicated by the presence of rotational isomers of the amide group.

3.00–3.20 (4H, complex); 3.44 (1H, dd); 3.68 and 3.92 (combined, 2H, apparent broad singlets); 3.99 and 4.27 (Combined, 2H, apparent broad singlets); 4.45 ($^1$H, dd); 6.70–7.50 (9H, complex); and 8.78 (1H, br s, exchanges with D$_2$O).

Example 3

5-(4-[2-(N-(5-Chloro-2-methoxybenzoyl)amino)ethoxy]-benzylidene) -2,4-thiazolilidinedione.

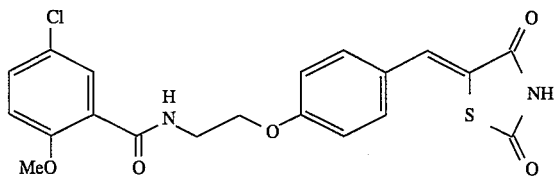

The title compound, mp 213-4° C., was prepared from 4-[2-(N-(5-chloro- 2-methoxybenzoyl)amino)ethoxy]benzaldehyde (1.7 g) by a method similar to that described in Example 1.

$^1$H NMR δ (DMSO-d$_6$)

3.66 (2H, complex); 3.86 (3H, s); 4.19 (2H, t); 7.15 (3H, complex); 7.45–7.80 (5H, complex), 8.47 (1H, br, exchanges with D$_2$O); and 12.50 (1H, br, exchanges with D$_2$O).

Example 4

5-(4-[2-(N-(5-Chloro-2-methoxybenzoyl)amino)ethoxy]benzyl)-2,4-thiazolidinedione.

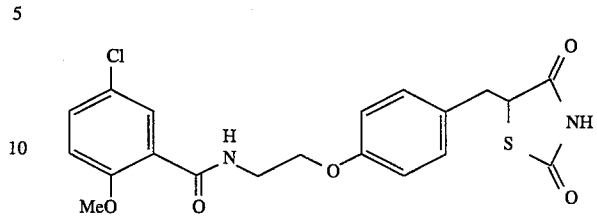

5-(4-[2-(N-(5-Chloro-2-methoxybenzoyl)amino)ethoxy]-benzylidene)-2,4-thiazolidinedione (1.7 g) was dissolved in dioxan (80 ml) and hydrogenated for a total of 22 hours in a manner similar to that described in Example 2. The title compound was obtained as a foam, mp 66-67° C.

$^1$H NMR δ (DMSO-d$_6$)

3.06 (1H, dd); 3.31 (1H, dd); 3.65 (2H, complex); 3.87 (3H, s); 4.09 (2H, t); 4.87 (1H, dd); 6.92 (2H, d); 7.17 (3H, apparent d); 7.52 (1H, dd); 7.71 (1H, d); 8.45 (1H, t, exchanges with D$_2$O); and 12.03 (1H, br s, exchanges with D$_2$O).

Example 5

5-(4-[2-(N-Methyl-N-phenylacetylamino)ethoxy]-benzylidene)-2,4-thiazolidinedione.

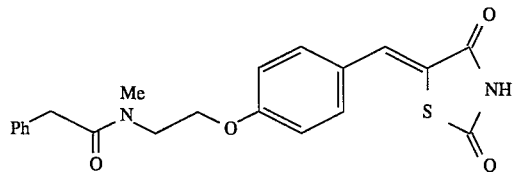

The title compound, mp 145-8° C., was prepared from 4-[2-(N-methylphenylacetylamino)ethoxy] benzaldehyde (5.6 g) by a procedure analogous to that described in Example 1.

$^1$H NMR δ (CDCl$_3$/DMSO-d$_6$; 1:1)

This spectrum is complicated by the presence of rotational isomers of the amide group.

3.02 and 3.15 (combined 3H, singlets); 3.65–3.90 (4H, complex); 4.15 (2H, complex); 7.00 (2H, br d); 7.10–7.60 (7H, complex); 7.77 (1H,s); and 12.20 (1H, br s, exchanges with D$_2$O).

Example 6

5-(4-[2-(N-Methyl-N-phenylacetylamino)ethoxy]benzyl)- 2,4,thiazolidinedione.

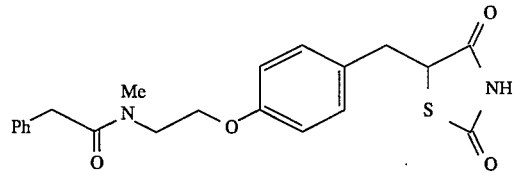

5-(4-[2-(N-Methyl-N-phenylacetylamino)ethoxy]benzylidene)- 2,4,thiazolidinedione (5.75 g) was dissolved in dioxan (450 ml) and hydrogenated for a total of 48 hours in a manner analogous to that described in Example 2. The title compound, a foam mp 45-9° C., was obtained following chromatography of the reaction mixture on silica gel with 1.5% methanol in dichloromethane as solvent.

$^1$H NMR δ (DMSO-$d_6$; 120° C.)

This spectrum is complicated by the presence of rotational isomers of the amide group. These coalesce at 120° C.

2.99 (3H, s); 3.06 (1H, dd); 3.32 (1H, dd); 3.67 (2H, t); 3.70 (2H, s); 4.09 (2H, t); 4.75 (1H, dd); 6.84 (2H, d); 7.05–7.35 (7H complex); and 12.00 (1H, s exchanges with $D_2O$).

Example 7

5-(4-[2-(N-Methyl-N-(2-pyridyl)acetylamino)ethoxy] benzylidene)-2,4-thiazolidinedione

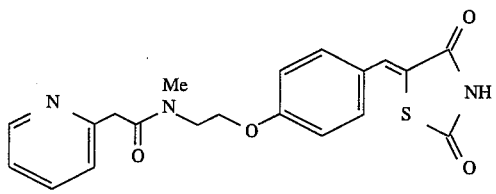

The title compound, mp 232-234° C. was prepared from 4-[2-(N-methyl-N-( 2-pyridyl)acetylamino)ethoxy]benzaldehyde (5.59 g) by a method similar to that described in Example 1.

$^1$H NMR δ ($CF_3CO_2D$)

This spectrum is complicated by the presence of rotational isomers of the amide group.

3.20 and 3.42 (combined, 3H, singlets); 3.80–4.45 (4H, complex); 4.47 and 4.70 (combined, 2H, singlets); 7.05 (2H, d); 7.55 (2H, d); 7.90–8.15 (3H, complex); 8.60 (1H, broad apparent triplet); and 8.85 (1H, d). The imide proton exchanges with the solvent.

Example 8

5-(4-[2-(N-Methyl-N-(2-pyridyl)acetylamino)ethoxy]-benzyl)-2,4-thiazolidinedione

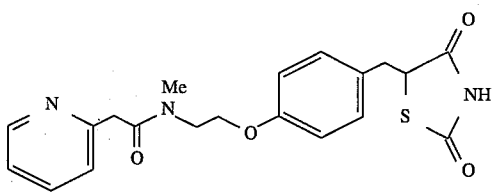

5-(4-[2-(N-Methyl-N-(2-pyridyl)acetylamino)ethoxy] benzylidene)-2,4-thiazolidinedione (5.25 g) was suspended in dioxan (400 ml) and hydrogenated over 10% palladium-charcoal (11.5 g total) for a total of 45 hours in a manner analogous to that described in Example 2. The reaction mixture was filtered and evaporated and the residue triturated with a boiling mixture of dichloromethane-hexane (3:1; 100 ml) to afford the title compound as a solid, mp 147 - 160° C. $^1$H NMR analysis showed this material to contain 10% by weight of unreduced benzylidene precursor.

$^1$H NMR δ (DMSO-$d_6$; 140° C.)

This spectrum is complicated by the presence of rotational isomers of the amide group. These coalesce at 140° C.

3.00–3.15 (4H, complex); 3.29 (1H, dd); 3.73 (2H, t); 3.86 (2H, s); 4.11 (2H, t); 4.73 (1H, dd); 6.85 (2H, d); 7.00–7.70 (5H, complex); 8.42 (1H, dd); and 11.50 (1H, br s, exchanges with $D_2O$).

In addition, this spectrum shows peaks corresponding to 0.1 equivalent of the benzylidene precursor (Example 7).

Example 9

5-(4-[2-(2,3-Dihydro-1H-isoindol-1-on-2-yl)ethoxy]benzylidene)-2,4-thiazolidinedione

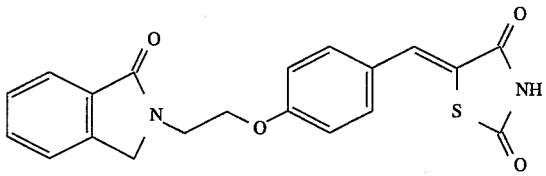

The title compound, mp 229-230° C., was prepared from 4-[2-(2,3-dihydro- 1H-isoindol-1-on-2-yl)ethoxy]-benzaldehyde (3.8 g) by a procedure analogous to that described in Example 1.

$^1$H NMR δ ($CDCl_3$/DMSO-$d_6$; 1:1)

4.00 (2H, t); 4.30 (2H, t); 4.62 (2H, s); 7.00–7.80 (9H, complex); and 12.40 (1H, br s, exchanges with $D_2O$).

Example 10

5-(4-[2-(2,3-Dihydro-1H-isoindol-1-on-2-yl)ethoxy]benzyl)-2,4-thiazolidinedione

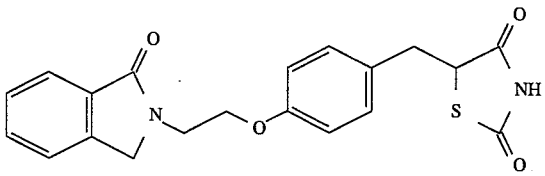

5-(4-[2-(2,3-Dihydro-1H-isoindol-1-on-2-yl)ethoxy]benzylidene)-2,4-thiazolidinedione (3 g) was suspended in dioxan (250 ml) and hydrogenated over 10% palladium-charcoal (6 g total) for 51 hours by a method analogous to that described in Example 2. The mixture was filtered and the solvent evaporated to afford a solid. Recrystallisation from dichloromethane-hexane gave the title compound, mp 153-5° C.

$^1$H NMR δ ($CDCl_3$)

3.09 (1H, dd); 3.42 (1H, dd); 4.01 (2H, t); 4.20 (2H, t); 4.47 (1H, dd); 4.62 (2H, s); 6.84 (2H, d); 7.14 (2H,d); 7.40–7.60 (3H, complex); 7.85 (1H, d); and 8.91 (1H, br s, exchanges with $D_2O$).

Example 11

5-[4-[3-(2,3-Dihydro-1H-isoindol-1-on-2-yl)propoxy] benzylidene]-2,4-thiazolidinedione.

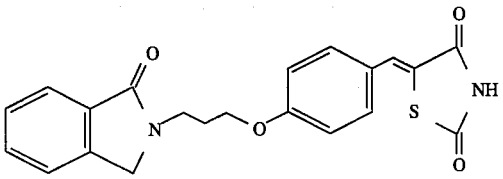

The title compound, mp 260-263° C., was prepared from 4-[3-(2,3-dihydro- 1H-isoindol-1-on-2-yl)propoxy]benzaldehyde (4.22 g) by a method anaolgous to that described in Example 1.

$^1$H NMR δ (CDCl$_3$)

2.09 (2H, complex); 3.70 (2H, t); 4.10 (2H, t); 4.52 (2H, s); 7.07 (2H, d); 7.45–7.80 (7H, complex); and 12.49 (1H, br s, exchanges with D$_2$O).

Example 12

5-[4-[3-(2,3-Dihydro-1H-isoindol-1-on-2-yl)propoxy] benzyl]-2,4-thiazolidinedione

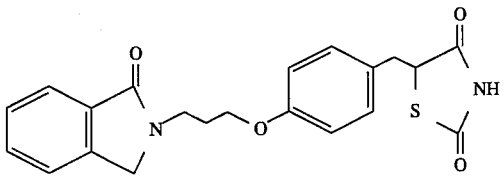

The title compound, mp 135-8° C., was prepared from 4-[3-(2,3-dihydro-1H-isoindol- 1-on-2-yl)propoxy]benzylidine]-2,4-thiazolidinedione (4.00 g) by a method analogous to that described in Example 10.

$^1$H NMR δ (DMSO-d$_6$)

2.05 (2H, complex); 3.02 (1H,dd); 3.27 (1H, dd); 3.68 (2H, t); 3.99 (2H, t); 4.51 (2H,s); 4.86 (1H, dd); 6.85 (2H, d); 7.12 (2H, d); 7.40–7.75 (4H, complex); and 12.02 (1H, br s).

Example 13

5-[4-[2-(3,4-Dihydro-2H-isoquinolin-1-on-2-yl)ethoxy] benzylidene]-2,4-thiazolidinedione

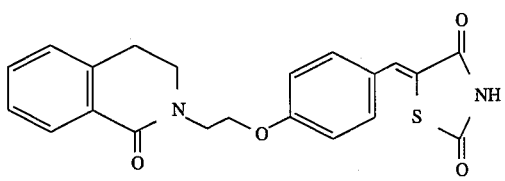

The title compound, mp 180-183° C., was prepared from 4-[2-(3,4-dihydro- 2H-isoquinolin-1-on-2-yl)ethoxy]benzaldehyde (4.21 g) by a method analogous to that described in Example 1.

$^1$H NMR δ (CDCl$_3$/DMSO-d$_6$; 1:1)

2.89 (2H, apparent t); 3.40–4.00 (4H, complex); 4.20 (2H, t); 6.85–8.00 (9H, complex); and 12.35 (1H, broad singlet, exchanges with D$_2$O).

Example 14

5-[4-[2-(3,4-Dihydro-2H-isoquinolin-1-one-2-yl)ethoxy] benzyl]-2,4-thiazolidinedione

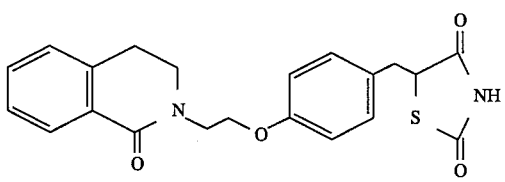

The title compound, mp 136-9° C., was prepared from 5-[4-[2-(3,4-dihydro- 2H-isoquinolin-1-one-2-yl )ethoxy] benzylidene]-2,4-thiazolidinedione (4.4 g) by a method analogous to that described for Example 2.

$^1$H NMR δ (DMSO-d$_6$)

2.95 (2H, t); 3.03 (1H, dd); 3.27 (1H, dd); 3.67 (2H, t); 3.83 (2H, t); 4.16 (2H, t); 4.84 (1H, dd); 6.91 (2H, d); 7.14 (2H, d); 7.25–7.55 (3H, complex); 7.87 (1H, d); and 12.00 (1H, broad s; exchanges with D$_2$O).

Example 15

5-[4-[2-[N-Methyl-N-(3-phenylpropanoyl)amino]ethoxy] benzylidene]-2,4-thiazolidinedione

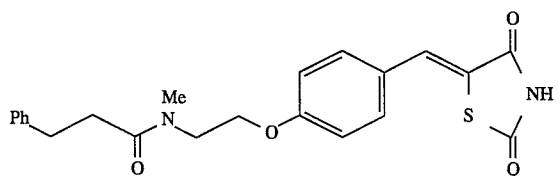

The title compound, mp 172-5° C., was prepared from 4-[2-[N-methyl-N-(3-phenylpropanoyl)amino] ethoxy]benzaldehyde (3.17 g) by a method analogous to that described in Example 1.

$^1$H NMR δ (CDCl$_3$)

This spectrum is complicated by the presence of rotational isomers of the amide group.

2.50–3.00 (4H, complex); 2.95 and 3.10 (combined, 3H, singles); 3.75 (2H, apparent broad t); 4.20 (2H, complex); 6.85–7.60 (9H, complex); 7.75 (1H, s); and 11.50 (1H, broad s).

Example 16

5-[4-[2-[N-Methyl-N-(3-phenylpropanoyl)amino]ethoxy]benzyl]-2,4-thiazolidinedione.

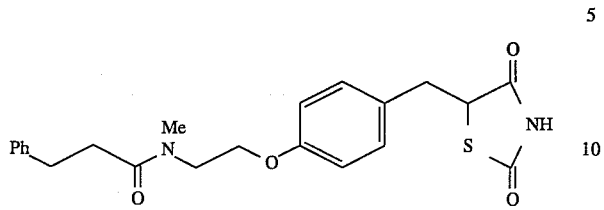

The title compound, a foam mp 50° C., was prepared from 5-[4-[2-[N-methyl-N-( 3-phenylpropanoyl)amino]ethoxy]benzylidene]-2,4-thiazolidinedione (3.50 g) in a manner analogous to that described for Example 2.

$^1$H NMR δ (DMSO-$d_6$/$D_2O$); 120° C.

This spectrum is complicated by the presence of rotational isomers of the amide group. These coalesce at 120° C.

2.63 (2H, t); 2.86 (2H, t); 2.94 (3H, s); 3.06 (1H, dd); 3.30 (1H, dd); 3.64 (2H, t); 4.07 (2H, t); 4.73 (1H, dd); 6.85 (2H, d); 7.05–7.30 (7H, complex).

DEMONSTRATION OF EFFICACY OF COMPOUNDS

Obese Mice, Oral Glucose Tolerance Test

C57bl/6 obese (ob/ob) mice were fed on powdered oxoid diet. After at least one week, the mice continued on a powdered oxoid diet or were fed powdered oxoid diet containing the test compound. After 8 days on the supplemented diet all of the mice were fasted for 5 hours prior to receiving an oral load of glucose (3 g/kg). Blood samples for glucose analysis were taken 0, 45, 90 and 135 minutes after glucose administration and the results appear below as the percentage reduction in area under the blood glucose curve where test compound treated groups are compared with the control groups. 7 mice were used for each treatment.

| EXAMPLE NO: | LEVEL IN DIET (mmol kg$^{-1}$ of DIET) | % REDUCTION IN AREA UNDER BLOOD GLUCOSE CURVE |
|---|---|---|
| 2 | 300 | 19 |
| 4 | 1000 | 27 |
| 6 | 300 | 52 |
| 8 | 300 | 32 |
| 10 | 300 | 44 |
| 12 | 1000 | 32 |
| 14 | 300 | 29 |
| 16 | 300 | 17 |

Toxicology

No toxicological effects were indicated for any of the compounds of the invention in any of the abovementioned tests.

We claim:

1. A compound of formula (I):

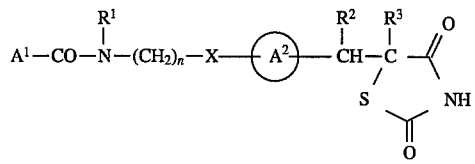

or a tautomeric form thereof and/or a pharmaceutically acceptable salt thereof, and a pharmaceutically acceptable solvate thereof, wherein:

$A^1$ represents an alkyl group, a substituted or unsubstituted aryl group, an aralkyl group wherein the alkylene or the aryl moiety may be substituted or unsubstituted;

$A^2$ represents a benzene ring having in total up to three optional substituents;

$R^1$ represents a hydrogen atom, an alkyl group, or an aralkyl group wherein the alkyl or the aryl moiety may be substituted or unsubstituted;

$R^2$ and $R^3$ each represent hydrogen, or $R^2$ and $R^3$ together represent a bond;

X represents O or S; and n represents an integer in the range of from 2 to 6.

2. A compound according to claim 1, wherein $A^2$ represents a moiety of formula (a):

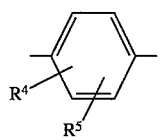

(a)

wherein $R^4$ and $R^5$ each independently represent hydrogen, halogen, substituted or unsubstituted alkyl or alkoxy.

3. A compound according to claim 1, wherein $R^1$ represents a methyl group.

4. A compound according to claim 1, wherein $R^2$ and $R^3$ each represent hydrogen.

5. A compound according to claim 1, selected from the list consisting of:

5-(4-[2-(N-benzoyl-N-methylamino)ethoxy]benzylidene)-2,4-thiazolidinedione;

5-(4-[2-(N-benzoyl-N-methylamino)ethoxy]benzyl)-2,4-thiazolidinedione;

5-(4-[2-(N-(5-chloro-2-methoxybenzoyl)amino)ethoxy]-benzylidene)-2,4-thiazolidinedione;

5-(4-[2-(N-(5-chloro-2-methoxybenzoyl)amino)ethoxy]benzyl)-2,4-thiazolidinedione;

5-(4-[2-(N-methyl-N-phenylacetylamino)ethoxy]-benzylidene)-2,4-thiazolidinedione;

5-(4-[2-(N-methyl-N-phenylacetylamino)ethoxy]benzyl)- 2,4,thiazolidinedione;

5-[4-[2-[N-methyl-N-(3-phenylpropanoyl)amino]ethoxy]benzylidene]-2,4-thiazolidinedione; and 5-[4-[2-[N-methyl-N-(3-phenylpropanoyl)amino]ethoxy]benzyl]-2,4-thiazolidinedione; or a tautomeric form thereof or a pharmaceutically acceptable salt thereof or a pharmaceutically acceptable solvate thereof.

6. A pharmaceutical composition comprising a compound according to claim 1, or a tautomeric form thereof, or a pharmaceutically acceptable salt thereof, or a pharmaceutically acceptable solvate thereof, and a pharmaceutically acceptable carrier therefor.

7. A method for the treatment of hyperglycaemia in a human or non-human mammal which comprises administering an effective, non-toxic, amount of a compound according to claim 1, or a tautomeric form thereof or a pharmaceutically acceptable salt thereof or a pharmaceutically acceptable solvate thereof to a hyperglycaemic human or non-human mammal in need thereof.

8. A method for the treatment of hyperlipidaemia, or hyperglycemia, in a human or non-human mammal, which comprises administering an effective, non-toxic, amount of a compound according to claim 1, or a tautomeric form thereof or a pharmaceutically acceptable salt thereof or a pharmaceutically acceptable solvate thereof, to a human or non-human mammal in need thereof.

9. A pharmaceutical composition comprising a compound according to claim 5 and a pharmaceutically acceptable carrier.

10. A method for the treatment of hyperlipidemia or hyperglycemia in a mammal which comprises administering an effective, non-toxic amount of a compound according to claim 5.

* * * * *